United States Patent [19]  
Riddle

[11] 4,064,182  
[45] Dec. 20, 1977

[54] PREPARATION OF SECONDARY ALKANOL ALKOXYLATES

[75] Inventor: John L. Riddle, Humble, Tex.

[73] Assignee: Continental Oil Company, Ponca City, Okla.

[21] Appl. No.: 761,184

[22] Filed: Jan. 21, 1977

Related U.S. Application Data

[63] Continuation-in-part of Ser. No. 597,845, July 21, 1975, abandoned.

[51] Int. Cl.² .................................................. C07C 41/02
[52] U.S. Cl. ........................................................ 260/615 B
[58] Field of Search ............................ 260/615 B, 615 R

[56] References Cited

U.S. PATENT DOCUMENTS

| | | | |
|---|---|---|---|
| 2,481,278 | 9/1949 | Ballard et al. | 260/615 B |
| 2,492,955 | 1/1950 | Ballard et al. | 260/615 B |
| 2,510,540 | 6/1950 | Ballard et al. | 260/615 B |
| 2,520,733 | 8/1950 | Morris et al. | 260/615 B |
| 2,870,220 | 1/1959 | Carter | 260/615 B |
| 3,117,998 | 1/1964 | Cosby et al. | 260/615 B X |
| 3,190,927 | 6/1965 | Patton et al. | 260/615 B X |
| 3,346,557 | 10/1967 | Patton et al. | 260/615 B X |
| 3,393,219 | 7/1968 | Myerly et al. | 260/615 B X |
| 3,489,690 | 1/1970 | Lachampt | 260/615 B |
| 3,935,279 | 1/1976 | Cocuzza et al. | 260/615 B |

FOREIGN PATENT DOCUMENTS 722,733  11/1965  Canada .............................. 260/615 B

*Primary Examiner*—Howard T. Mars  
*Attorney, Agent, or Firm*—Bayless E. Rutherford, Jr.

[57] ABSTRACT

An improved process for preparing high mole secondary alkanol alkoxylates by the reaction of low mole secondary alkanol alkoxylates with an alkylene oxide in the presence of caustic is disclosed. The improvement comprises use of a hydrogen-treated low mole secondary alkanol alkoxylate.

6 Claims, No Drawings

PREPARATION OF SECONDARY ALKANOL ALKOXYLATES

CROSS-REFERENCE TO RELATED APPLICATIONS

The present application is a continuation-in-part of application Ser. No. 597,845, filed July 21, 1975 and now abandoned.

BACKGROUND

1. FIELD OF THE INVENTION

The invention is in the field of preparing improved high mole secondary alkanol alkoxylates.

General Background

The use of alkoxylates from secondary alkanols in liquid detergent formulations is well known. These secondary alkanol alkoxylates are prepared by reacting an alkylene oxide with the secondary alkanol in the presence of a catalyst. One such process for preparing the secondary alkanol alkoxylate is a two-step process. In the two-step process a Lewis acid (e.g. boron trifluoride, or aluminum chloride) is used in the first step, while a strong base (e.g. sodium hydroxide) is used in the second step. In this process, a low mole alkoxylate is produced in the first step. In the second step, the low mole alkoxylate, which usually has been stripped to remove alcohol, is reacted with additional alkylene oxide to produce the desired product.

In conducting the first step, the low mole product contains "impurities." Such a product when subjected to a caustic-catalyzed second step results in a high mole alkoxylate having a color which varies from pale to dark yellow, and, consequently, is undesirable.

My invention is directed to an improvement which results in high mole alkoxylates having improved colors. Briefly, I have found that hydrogen-treating the low mole alkoxylate, prior to conducting the second step, results in a final product having improved color. By contrast, hydrogen-treating of the final product prepared by the two-step process does not result in any color improvement.

2 PRIOR ART

A search of the prior art produced four references which are considered to be only of general interest with regard to the present invention. In order to provide a complete disclosure these references will be discussed briefly.

U.S. Pat. No. 3,359,250 teaches the decolorization of dipentene polymer by the hydrogenation thereof.

U.S. Pat. No. 3,040,076 teaches that the addition of reducing agents to alkoxylation reaction mixtures improves the color of the final product.

U.S. Pat. No. 2,983,763 teaches a process for improving the polyether products, particularly the color thereof, resulting from reacting an alkylene oxide with a hydroxyl-containing organic compound in the presence of a catalyst such as sodium hydroxide. The process comprises adding an acidic substance (e.g. phosphoric acid) to the reaction prior to separation from the catalyst.

U.S. Pat. No. 3,168,569 teaches a method of bleaching polyalkylene ethers wherein the method uses an alkali metal borohydride as the bleaching agent.

BRIEF SUMMARY OF THE INVENTION

Briefly stated, the present invention is directed to an improvement in the process of preparing high mole secondary alkanol alkoxylates by the reaction of low mole secondary alkanol alkoxylates with an alkylene oxide in the presence of caustic wherein the improvement comprises use of a hydrogen-treated low mole secondary alkanol alkoxylate.

In a preferred aspect, the present invention is directed to an improvement in the process of preparing high mole secondary alkanol alkoxylates by the reaction of a low secondary alkanol alkoxylate with an alkylene oxide in the presence of caustic catalyst wherein the improvement comprises conducting the process with a low mole secondary alkanol alkoxylate which has been reacted with hydrogen under pressure in the presence of a hydrogenation catalyst.

DETAILED DESCRIPTION

The alkoxylates used in the process of my invention are derived from secondary alkanols containing from about 6 to about 20, preferably from about 10 to about 15, carbon atoms. The hydroxyl group is randomly located on the carbon chain. Predominantly, the hydroxyl group is on internal carbon atoms, although there can be a minor amount of terminal carbon atoms containing a hydroxyl group.

The alkylene oxides which are used to prepare the alkoxylates can be represented by the formula

wherein R' is hydrogen or a $C_1$–$C_5$ alkyl group. Ethylene oxide is the preferred alkylene oxide. Other suitable alkylene oxides are propylene oxide, butylene oxide, and pentylene oxide.

Using an internal secondary alkanol, the alkoxylates can be illustrated by the following formula

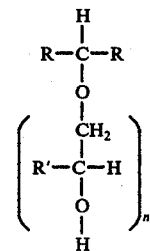

wherein R' is as defined above, $n = 1$ to 30, and wherein R is a $C_1$ to $C_{18}$ alkyl group, with the sum of both R groups containing 5 to 19 carbon atoms.

The term low mole alkoxylate refers to those wherein n is 1 to 4.9, with an average of about 3. The term high mole alkoxylates refers to those wherein $n = 5$ to 30, preferably 7 to 12.

The caustic catalyzed alkoxylation of low mole alkanol alkoxylates is well-known in the art. While any strong base can be used, for reason for economy sodium hydroxide is usually employed. The amount of sodium hydroxide typically is in the range of 0.05 to 0.5 weight percent of the low mole alkoxylate.

In conducting the hydrogen treatment, the low mole alkoxylate is added to an autoclave or continuous hydrogenation unit. A typical hydrotreating catalyst (e. g. nickel) is then added to the reaction vessel. Hydrogen is then added to attain the desired pressure. Suitable temperature and pressure ranges are 100°–170° C. and 34–136 atmosphere, respectively. Preferred temperature and pressure ranges are 130°–150° C. and 54–68 atmosphere, respectively.

Any of the known hydrogenation catalysts can be used in the hydrogen treatment step. Examples of suitable catalysts include Raney nickel catalysts and noble metal catalysts such as platinum, platinum oxide, palladium and palladium oxide. A more complete discussion of catalysts is provided in U.S. Pat. No. 3,359,250, which discussion is made a part of this disclosure.

The amount of catalysts is usually in the range of about 0.1 to about 10.0 weight percent, more usually about 0.5 to about 5 weight percent, based on the low mole alkoxylate.

Generally, the hydrogen pressure is maintained on the autoclave for about 2 hours. While longer times can be used (e.g. up to 10 hours) they generally are not used for economic reasons. Again, any person skilled in the art can determine the optimum time for hydrogen treating, without resorting to undue experimentation.

At the end of the hydrogen-treating time period, the hydrogen is vented and the autoclave is allowed to cool to about room temperature. On recovering the liquid product from the autoclave, it is filtered (e.g. by passing through a diatomaceous earth filter aid) to remove catalyst.

In order to disclose the nature of the present invention more specifically, the following examples, both illustrative and comparative, will be given. It is to be understood that the invention is not to be limited to the specific conditions or details set forth in these examples except insofar as these limitations are specified in the appended claims.

EXAMPLE 1

This example illustrates the improvement obtained by hydrogen-treating the low mole alkoxylate.

The alkoxylates used were ethoxylates of $C_{12}$–$C_{14}$ secondary alkanols, containing about 3 moles of ethylene oxide. The alkoxylates had APHA colors of about 10–15.

The hydrogen-treating procedure was as follows: The low mole ethoxylates and 2 weight percent nickel catalysts were placed in an autoclave. The autoclave was positively pressured with hydrogen, then the temperature was raised 115° C. When the temperature had stabilized, the hydrogen pressure was increased to 54 atmospheres. The hydrogen pressure was maintained for two hours, then the autoclave was allowed to cool. The hydrogen was vented and the treated liquid was filtered through "Hyflo" (diatomaceous earth filter aid) to remove catalyst.

The hydrogen-treated low mole ethoxylate was then converted to a high mole ethoxylate (containing 9 moles ethylene oxide) by reaction with ethylene oxide using sodium hydroxide as the catalyst.

For purpose of comparison a sample of the low mole ethoxylate, which had not been treated with hydrogen, was converted to high mole ethoxylate using the same procedure.

The results of a series of five runs are shown below.

|  | APHA Color* | |
|---|---|---|
|  | Not Treated | Hydrogen-Treated |
| Run A | 80 | 35 |
| Run B | 100 | 35 |
| Run C | 65 | 25 |
| Run D | 80 | 65 |
| Run E | 50 | 35 |

*As determined by ASTM Method D-1209

As is apparent in all cases the hydrogen-treated material had a lower color. The differences in color of the "not treated" materials are due to minor variations in final processing of the "parent" alcohols.

EXAMPLE 2

This example illustrates the improvement obtained using hydrogen-treated low mole ethoxylates to prepare high mole ethoxylates which contained differing amounts of ethylene oxide.

The low mole ethoxylates contained about 3 moles ethylene oxide and had an APHA color of less than 10. They were treated with hydrogen using the procedure of Example 1.

The low mole ethoxylate was converted to the high mole ethoxylate using sodium hydroxide as the catalyst.

The secondary alcohol used, the moles of ethylene oxide and the APHA color from the various runs are shown below.

| Run No. | Alcohol | Moles EO*/Moles ROH | APHA Color |
|---|---|---|---|
| A | $C_{10}$–$C_{12}$ | 4.7 | 30 |
| B | $C_{12}$–$C_{14}$ | 5.1 | 20 |
| C | $C_{12}$–$C_{14}$ | 6.9 | 10 |
| D | $C_{12}$–$C_{14}$ | 7.25 | 20 |
| E | $C_{12}$–$C_{14}$ | 8.6 | 10 |
| F | $C_{12}$–$C_{14}$ | 9.0 | 30 |

*EO = ethylene oxide

EXAMPLE 3

This example is both illustrative and comparative. The example shows the following:
A. Hydrogen-treating of low-mole ethoxylate results in an improved color in the high-mole ethoxylate, as compared to material which has not been hydrogen-treated.
B. Hydrogen-treating of high-mole ethoxylate, prepared by two-step procedure and wherein the low-mole ethoxylate has not been hydrogen-treated, does not result in improved color.
C. Hydrogen-treating of high-mole ethoxylate, prepared from low-mole ethoxylate which has been hydrogen-treated, does not result in improved color.

The alkoxylates used were ethoxylates of $C_{12}$–$C_{14}$ secondary alkanols prepared using $BF_3$ catalyst and contained about 3 moles ethylene oxide.

The second-stage ethoxylation was conducted using the ethoxylate described in the preceding and using NaOH as the catalyst. The resulting product contained about 8 moles ethylene oxide.

The hydrogen-treating was conducted using nickel as the catalyst (60% Ni on $Al_2O_3$) in a continuous process. The conditions were as follows:
$H_2$ Pressure — 800 psig
Temperature — 150° C.
Ethoxylate catalyst ratio (WHSV.) = 1

*WHSV = weight hourly space velocity

Hydrogen-treating was conducted on the following:
a. low-mole ethoxylate
b. high-mole ethoxylate which was not prepared from hydrogen-treated low-mole ethoxylate
c. high-mole ethoxylate which was prepared from hydrogen-treated treated low-mole ethoxylate.

The results were as follows:

| | | Color | |
|---|---|---|---|
| A. | Use of non-hydrogen-treated low-mole ethoxylate | APHA | Klett |
| 1. | Low-mole ethoxylate (per se) | 30 | 11 |
| 2. | High-mole ethoxylate | 80 | 53 |
| 3. | High-mole ethoxylate after being hydrogen-treated | 100 | 74 |
| B. | Use of hydrogen-treated low-mole ethoxylate | | |
| 1. | Hydrogen-treated low-mole ethoxylate (per se) | 20 | 4 |
| 2. | High-mole ethoxylate (per se) | 30 | 14 |
| 3. | High-mole ethoxylate after being hydrogen-treated | 30 | 11 |

Comparison of samples B-2, A-2 and A-3 clearly show the advantages of my invention.

Thus, having described the invention in detail, it will be understood by those skilled in the art that certain variations and modifications may be made without departing from the spirit and scope of the invention as defined herein and in the appended claims.

I claim:

1. In a process for preparing high mole secondary alkanol alkoxylates by the reaction of a low mole secondary alkanol alkoxylate with an alkylene oxide in the presence of a caustic catalyst, the improvement comprising conducting the process with a low mole secondary alkanol alkoxylate which has been reacted with hydrogen under pressure in the presence of a hydrogenation catalyst, said process being characterized further in that the terms low mole and high mole refer to numbers in the range of 1 to 4.9 and 5 to about 30, respectively and wherein said alkylene oxide is represented by the formula

wherein R' is hydrogen or a $C_1$–$C_5$ alkyl group, wherein the hydrogen treatment is conducted at a temperature in the range of about 100° to about 170° C and a hydrogen pressure in the range of about 34 to about 136 atmospheres.

2. The process of claim 1 wherein the low mole secondary alkanol alkoxylate is derived from a secondary alkanol containing about 6 to about 20 carbon atoms.

3. The process of claim 2 wherein the temperature is in the range of about 130° to about 150° C. and the pressure is in the range of about 54 to about 68 atmospheres.

4. The process of claim 3 wherein a secondary alkanol containing about 10 to about 15 carbon atoms is used to prepare the low mole secondary alkanol alkoxylate.

5. The process of claim 1 wherein a nickel catalyst is used in the hydrogen treatment of the low mole secondary alkanol alkoxylate.

6. The process of claim 4 wherein the alkylene oxide is ethylene oxide.

* * * * *

UNITED STATES PATENT OFFICE
CERTIFICATE OF CORRECTION

PATENT NO. : 4,064,182
DATED : December 20, 1977
INVENTOR(S) : John L. Riddle

It is certified that error appears in the above-identified patent and that said Letters Patent are hereby corrected as shown below:

Column 1, line 64, after the word reaction "product" was omitted.

Column 2, line 14, after the word low "mole" was omitted.

Signed and Sealed this

Sixth Day of June 1978

[SEAL]

Attest:

RUTH C. MASON
Attesting Officer

DONALD W. BANNER
Commissioner of Patents and Trademarks